United States Patent
Lawrence et al.

(10) Patent No.: US 9,375,405 B2
(45) Date of Patent: *Jun. 28, 2016

(54) RAPID DISSOLUTION FORMULATION OF A CALCIUM RECEPTOR-ACTIVE COMPOUND

(75) Inventors: Glen Gary Lawrence, Thousand Oaks, CA (US); Francisco J. Alvarez, Newbury Park, CA (US); Hung-Ren H. Lin, Oak Park, CA (US); Tzuchi R. Ju, Vernon Hills, IL (US)

(73) Assignee: Amgen, Inc., Thousand Oaks, CA (US)

( * ) Notice: Subject to any disclaimer, the term of this patent is extended or adjusted under 35 U.S.C. 154(b) by 1190 days.

This patent is subject to a terminal disclaimer.

(21) Appl. No.: 12/942,646

(22) Filed: Nov. 9, 2010

(65) Prior Publication Data

US 2011/0136915 A1 Jun. 9, 2011

Related U.S. Application Data

(63) Continuation of application No. 10/937,870, filed on Sep. 10, 2004, now Pat. No. 7,829,595.

(60) Provisional application No. 60/502,219, filed on Sep. 12, 2003.

(51) Int. Cl.
*A61K 31/135* (2006.01)
*A61K 31/137* (2006.01)
*A61K 31/00* (2006.01)
*A61K 9/20* (2006.01)
*A61K 9/28* (2006.01)

(52) U.S. Cl.
CPC ............ *A61K 31/00* (2013.01); *A61K 9/2077* (2013.01); *A61K 31/135* (2013.01); *A61K 31/137* (2013.01); *A61K 9/2866* (2013.01)

(58) Field of Classification Search
CPC ........................... A61K 31/135; A61K 31/137
USPC ................ 514/275, 579, 607, 614, 646, 649; 424/434, 464, 465, 476, 490
See application file for complete search history.

(56) References Cited

U.S. PATENT DOCUMENTS

| | | | |
|---|---|---|---|
| 4,931,286 A | 6/1990 | Johnson et al. | |
| 5,126,145 A | 6/1992 | Evenstad et al. | |
| 5,162,117 A | 11/1992 | Stupak et al. | |
| 5,861,179 A | 1/1999 | Hiskett et al. | |
| 5,879,706 A | 3/1999 | Carter et al. | |
| 5,981,599 A | 11/1999 | Moe et al. | |
| 6,001,884 A | 12/1999 | Nemeth et al. | |
| 6,011,068 A | 1/2000 | Nemeth et al. | |
| 6,031,003 A | 2/2000 | Nemeth et al. | |
| 6,172,091 B1 | 1/2001 | Cohen et al. | |
| 6,211,244 B1* | 4/2001 | Van Wagenen et al. | 514/649 |
| 6,224,909 B1 | 5/2001 | Opitz et al. | |
| 6,228,807 B1 | 5/2001 | Kuchikata et al. | |
| 6,277,788 B1 | 8/2001 | Wright | |
| 6,313,146 B1 | 11/2001 | Van Wagenen et al. | |
| 6,316,460 B1* | 11/2001 | Creekmore et al. | 514/275 |
| 6,342,532 B1 | 1/2002 | Moe et al. | |
| 6,363,231 B1 | 3/2002 | Manzer et al. | |
| 6,387,404 B2 | 5/2002 | Oshlack et al. | |
| 6,399,100 B1 | 6/2002 | Clancy et al. | |
| 6,419,954 B1 | 7/2002 | Chu et al. | |
| 6,432,656 B1 | 8/2002 | Del Mar et al. | |
| 6,447,809 B1 | 9/2002 | Krumhar et al. | |
| 6,495,165 B1 | 12/2002 | Thosar et al. | |
| 6,525,084 B2 | 2/2003 | Rasmussen et al. | |
| 6,656,492 B2* | 12/2003 | Kajiyama et al. | 424/434 |
| 6,733,780 B1 | 5/2004 | Tyler et al. | |
| 8,703,196 B2 | 4/2014 | Babcock et al. | |
| 2001/0051636 A1 | 12/2001 | Black et al. | |
| 2002/0015735 A1 | 2/2002 | Hedden et al. | |
| 2002/0022649 A1 | 2/2002 | Rasmussen et al. | |
| 2002/0107406 A1 | 8/2002 | Sakai et al. | |
| 2002/0123459 A1 | 9/2002 | Ault et al. | |
| 2003/0035836 A1 | 2/2003 | Shanghvi et al. | |
| 2003/0054041 A1 | 3/2003 | Lemmens et al. | |
| 2005/0147670 A1* | 7/2005 | Hsu et al. | 424/464 |

FOREIGN PATENT DOCUMENTS

| | | |
|---|---|---|
| CA | 2004565 A1 | 5/1990 |
| EP | 0 933 354 | 8/1999 |
| EP | 1319409 A1 | 6/2003 |
| EP | 1321142 A1 | 6/2003 |
| EP | 1 203 761 B1 | 1/2005 |
| JP | 11-130737 | 5/1999 |
| WO | WO 93/04373 | 3/1993 |

(Continued)

OTHER PUBLICATIONS

Japanese Pharmaceutical Excipients Directory by Yakuji Nippo, Ltd., 1994, 1st Ed., pp. 9 and 10.
Japanese Pharmaceutical Excipients, Supplement by Yakuji Nippo, Ltd., 1995, 1st Ed, p. 42.
Japanese Pharmaceutical Excipients, Supplement by Yakuji Nippo, Ltd., 1995, 1st Ed, p. 47.
Japanese Pharmaceutical Excipients, Supplement by Yakuji Nippo, Ltd., 1994, 1st Ed, p. 46.
Japanese Pharmaceutical Excipients, Supplement by Yakuji Nippo, Ltd., 1994, 1st Ed, p. 72.
Handbook of Pharmaceutical Excipients by Maruzen Co., Ltd., 1989, pp. 115-118.
The Notice of Rejection received in the related Japanese Patent Application No. 2006-526096, dated Jan. 11, 2011.
Amgen News Release, Internet Article "Amgen Submitted New Drug Application for Cinecalcet HC1", XP002313388, UR:: http://www.amgen.com/news/news03/pressRelease030908a.pdf, Sep. 8, 2003, 2 pages.

(Continued)

*Primary Examiner* — Michael G Hartley
*Assistant Examiner* — Jagadishwar Samala
(74) *Attorney, Agent, or Firm* — Fitzpatrick, Cella, Harper & Scinto

(57) ABSTRACT

The present invention relates to a pharmaceutical composition comprising a therapeutically effective amount of a calcium receptor-active compound and at least one pharmaceutically acceptable excipient, wherein the composition has a controlled dissolution profile. The present invention further relates to a method of manufacturing the pharmaceutical composition, as well as a method of treating a disease using the pharmaceutical composition.

23 Claims, 1 Drawing Sheet

(56) References Cited

FOREIGN PATENT DOCUMENTS

| WO | WO 94/18959 | 9/1994 |
|---|---|---|
| WO | WO 95/11221 | 4/1995 |
| WO | WO 96/12697 | 5/1996 |
| WO | WO 97/41090 | 11/1997 |
| WO | WO 01/34562 | 5/2001 |
| WO | 2004056365 A3 | 7/2004 |

OTHER PUBLICATIONS

Berge et al., "Pharmaceutical Salts," J. Pharm, Sci., Jan. 1917, pp. 1-19, vol. 66, No. 1.
Drugs in R&D, "Cinecalcet: AMG 073, Calcimimetics—Amgen/NPS Pharmaceuticals, KRN 1493, NPS 1493," 2003, pp. 349-351, vol. 4, No. 6.
Goodman et al., "The Calcimimetic Agent AMG 073 Lowers Plasma Parathyroid Hormone Levels in Hemodialysis Patients with Secondary Hyperparathyroidism," J. Am. Soc. Nephrol, Apr. 2002, pp. 1017-1024, vol. 13.
Nemeth et al., Pharmacodynamics of the Type II Calcimimetic Compound Cinacalcet HCI, J. Pharmacol. Exp Therapeutics, Feb. 2004, pp. 627-635, vol. 308, No. 2.
NPS Pharmaceuticals, Internet Article: "NPS Drug Development: Product Development Pipeline," XP-002313391, www.npsp.com/drug-development/pipline.php, Sep. 8, 2003, 2 pages, (retrieved by EPO Searching Authority on Jan. 12, 2005).
Pattaragarn et al., "Effect of the Calcimimetic NPS R-467 on Furosemide-Induced Nephrocalcinosis in the Young Rat," Kidney Internationa, 2004, pp. 1684-1689, vol. 65.
RxList, Inc., Internet Article: "Sensipar (Cinacalcet HCI) Tablets," XP-002313390, www.rxlist.com/cgi/generic3/sensipar.htm), Aug. 12, 2004, 2 pages, (retrieved by EPO Searching Authority on Jan. 10, 2015).
U.S. Food and Drug Administration, Internet Article: "FDA Approves First in a New Class of Drugs to Treat Hyperparathyroidism Associated with Renal Failure and in Patients with Parathyroid Cancer," FDA Talk Paper, XP-002313389, http://www.fda.gov/bbs/topics/ANSWERS/2004/ANS01282.html), Mar. 8, 2004, 1 page, (retrieved by EPO Searching Authority on Jan. 11, 2005).
European Patent No. EP1663182, Opposition document, Communication of a Notice of Opposition, dated Oct. 28, 2013—1 page.
European Patent No. EP1663182, Opposition document, Communication of a Notice of Opposition, dated Oct. 23, 2013—1 page.
European Patent No. EP1663182, Opposition document, Communication of a Notice of Opposition, dated Oct. 22, 2013—1 page.
European Patent No. EP1663182, Opposition document, Authorisation of Representative, Opponent: Rafarm S.A, dated Oct. 15, 2013—3 pages.
European Patent No. EP1663182, Opposition document, Letter Concerning Fees and Payment, Opponent: Rafarm S.A, dated Oct. 17, 2013—1 page.
European Patent No. EP1663182, Opposition document, Notice of Opposition, Opponent: Rafarm S.A, dated Oct. 17, 2013—8 pages.
European Patent No. EP1663182, Opposition document, Notice of Opposition, EPO Form 2300E, Opponent: Rafarm S.A., dated Oct. 15, 2013—12 pages.
European Patent No. EP1663182, Opposition document, Payment of Fees and Costs, Opponent: Rafarm S.A, dated Oct. 17, 2013—4 pages.
European Patent No. EP1663182, Opposition document, Acknowledgement of Receipt, Opponent: ZBM Patents, S.L., dated Oct. 16, 2013—2 pages.
European Patent No. EP1663182, Opposition document, Annex 1 "Grounds and Arguments filed by ZBM Patents, S.L. for the Opposition against the European patent EP1663182-B1 (App. No. 04781429.8) having Amgen Inc. as patentee, and Relating to a Rapid Dissolution Formulation of Cinacalcet Hydrochloride", dated Oct. 16, 2013—26 pages.
European Patent No. EP1663182, Opposition document, Notice of Opposition, EPO Form 2300E, Opponent: ZBM Patents, S.L., dated Oct. 16, 2013—6 pages.
European Patent No. EP1663182, Opposition document, Acknowledgement of Receipt, Opponent: Actavis Group PTC ehf, dated Oct. 14, 2013—2 pages.
European Patent No. EP1663182, Opposition document, Citation in Opposition Proceeding, "Scientific Discussion" filed Oct. 14, 2013—39 pages.
European Patent No. EP1663182, Opposition document, Notice of Opposition, Opponent: Actavis Group PTC ehf, dated Oct. 14, 2013—1 page.
European Patent No. EP1663182, Opposition document, Statement of Opposition, Opponent: Actavis Group PTC ehf, dated Oct. 14, 2013—15 pages.
European Patent No. EP1663182, Opposition document, Notice of Opposition, EPO Form 2300E, Opponent: Actavis Group PTCc ehf, dated Oct. 14, 2013—6 pages.
European Patent No. EP1663182, Opposition document, Patent Document Cited during Opposition Procedure on Oct. 14, 2013, "Decision of the Technical Board of Appeal 3.3.02 of Dec. 17, 2009", *Tecnimede Sociedade Tecnico-Medicinal, S.A. and Ratiopharm GmbH v. Sanofi-Aventis*, Case No. T 0788/06-3.3.02, Application No. 96304291.6, Publication No. 0747050, dated Dec. 17, 2009—24 pages.
European Patent No. EP1663182, Opposition document, Patent Document Cited during Opposition Procedure, Marked up Application No. PCT/US2004/026732, Publication No. WO 2005/034928, dated Nov. 11, 2010—42 pages.
Handbook of Pharmaceutical Excipients (1986) 2nd Ed. (1994) 483-487; 84-87; 143-144; 280-282; 392-399; 424-427; 491-493.
Handbook of Pharmaceutical Excipients (1986) 6th Ed. (2009) 129-131; 185-186; 208; 404; 581-582; 691-692.
Handbook of Pharmaceutical Excipients (1986) 3rd Ed. (2000) 528-529; 102-103; 433; 163-164; 305-306; 143; "Lactose"; "Calcium Phosphate, Dibasic Anhydrous" 324; 515; "Hydroxyproply Methylcellulose" 87; 244.
Goodman WG, et al. "The Calcimimetic Agent AMG 073 Lowers Plasma Parathyroid Hormone Levels in Hemodialysis Patients with Secondary Hyperparathyroidism", J Am Soc Nephrol (2002) 13: 1017-1024.
Franceschini N, et al. "Cinacalcet HCI: A Calcimimetic Agent for the Management of Primary and Secondary Hyperparathyroidism" Expert Opin Investig. Drugs (2003) 12(8): 1413-1421.
Lee K "Overview of Drug Product Development" Current Protocols in Phamacology (2001) 7.3.1-7.3.10.
Remington: The Science and Practice of Pharmacy (1885), 19th Ed. (1995) 595.
Remington: The Science and Practice of Pharmacy (1885), 20th Ed. (2000) 704-705, 858-893.
Lantz Jr. R "Size Reduction" Pharmaceutical Dosage Forms, Tablets, 2nd Ed. vol. 2, 107-112.
Banakar UV Pharmaceutical Dissolution Testing, (1992) 136-137; 144-145.
The Pharmaceutical Codex, 12th Ed. Principles and Practice of Pharmaceutics (1994) 2-23, 198-204.
Gibaldi M "Biopharmiceutics and Clinical Pharmacokinetics" (1991) 4th Ed. 51.
"Pharmaceuticals Necessities", Chap. 55 1047-1048.
Pharmaceutical Dosage Forms: Tablets vol. 1, 2nd Ed. (1989) 136, 149, 1-24.
The Theory and Practice of Industrial Pharmacy 3rd Ed. (1986) 221-222, 188-190, 301-303, 321, 324-329, 354-359.
Pharmaceutics the Science of Dosage Form Design (2002) 404-408.
European Patent No. EP1663182, Appeal document, EPO Form F3204 Communication of the File Number to the Parties, dated May 29, 2015—4 pages.
European Patent No. EP1663182, Appeal document, Processing of an Appeal, dated May 22, 2015—2 pages.
European Patent No. EP1663182, Appeal document, Letter Accompanying Subsequently Filed Items, dated May 20, 2015—1 page.
European Patent No. EP1663182, Appeal document, Notice of an Appeal, dated May 20, 2015—2 pages.

(56) References Cited

OTHER PUBLICATIONS

European Patent No. EP1663182, Appeal document, Payment of Fees and Costs, dated May 20, 2015—1 page.
European Patent No. EP1663182, Opposition document, Opponent 1's Request to Revoke Patent, dated Mar. 12, 2015—10 pages.
European Patent No. EP1663182, Opposition document, Decision to Revoke the European Patent, dated Feb. 23, 2015—26 pages.
European Patent No. EP1663182, Opposition document, Minutes of the Oral Proceeding, Conclusion of the Proceedings, dated Feb. 12, 2015—2 pages.
European Patent No. EP1663182, Opposition document, Minutes of the Oral Proceeding, Introduction of the Parties—dated Feb. 12, 2015—1 page.
European Patent No. EP1663182, Opposition document, Provision of the minutes in accordance with Rule 124(4) EPC, dated Mar. 12, 2015—1 page.
European Patent No. EP1663182, Opposition document, Annex 2, "Claims for 3rd Auxiliary Request", dated Feb. 12, 2015—3 pages.
European Patent No. EP1663182, Opposition document, Annex 3, "Claims for 4th Auxiliary Request", dated Feb. 12, 2015—2 pages.
European Patent No. EP1663182, Opposition document, Annex 1, "Auxiliary Request 2", dated Feb. 12, 2015—4 pages.
European Patent No. EP1663182, Opposition document, Communication from Party Regarding Non-attendance of Oral Hearing, dated Feb. 6, 2016—2 pages.
European Patent No. EP1663182, Opposition document, Information from EPO Regarding Oral Proceeding, dated Feb. 2, 2015—1 page.
European Patent No. EP1663182, Opposition document, Actavis Group Submission, dated Dec. 12, 2014—17 pages.
European Patent No. EP1663182, Opposition document, Acknowledgement of Receipt of Submission from Actavis, dated Dec. 11, 2014—1 page.
European Patent No. EP1663182, Opposition document, Letter from Actavis Group's Counsel Requesting Interpreter during Oral Hearing, dated Dec. 11, 2014—3 pages.
European Patent No. EP1663182, Opposition document, Letter from Amgen Inc.'s Counsel Requesting Interpreter during Oral Hearing, dated Dec. 11, 2014—3 pages.
European Patent No. EP1663182, Opposition document, Submission from Amgen Inc.'s Counsel in Preparation of Oral Proceeding, dated Nov. 21, 2014—15 pages.
European Patent No. EP1663182, Opposition document, Annex to an Opposition Letter, "Experimental Report II", filed Nov. 21, 2014—2 pages.
European Patent No. EP1663182, Opposition document, "Claims for New 5th Auxiliary Request", filed Nov. 11, 2014—3 pages.
European Patent No. EP1663182, Opposition document, "Claims for New 5th Auxiliary Request" (Redlined version), filed Nov. 11, 2014—4 pages.
European Patent No. EP1663182, Opposition document, Letter from Opponent 3 Advising of Non-attendance at Oral Proceedings, dated Oct. 20, 2014—6 pages.
European Patent No. EP1663182, Opposition document, Acknowledgement of Receipt of Submission from ZBM, dated Oct. 20, 2014—1 page.
European Patent No. EP1663182, Opposition document, Letter from Hoffmann Eitle, dated Sep. 26, 2014—2 pages.
European Patent No. EP1663182, Opposition document, Summary of Facts and Submissions, dated Jul. 18, 2014—5 pages.
European Patent No. EP1663182, Opposition document, Information Document from EPC Regarding Interpretation of Oral Proceeding, dated Jul. 18, 2014—3 pages.
European Patent No. EP1663182, Opposition document, Summons to Attend Oral Proceeding, dated Jul. 18, 2014—4 pages.
European Patent No. EP1663182, Opposition document, Preparation for Oral Proceedings—Instructions to Support Service, dated Jul. 2, 2014—2 pages.
European Patent No. EP1663182, Opposition document, Brief Communication Regarding Receipt of "Letter from the Proprietor of the Patent of May 28, 2014", dated Jun. 12, 2014—3 pages.
European Patent No. EP1663182, Opposition document, Annex to an Opposition Letter "Experimental Report", filed Jun. 3, 2014—1 page.
European Patent No. EP1663182, Opposition document, Annex to an Opposition Letter "Cited Documents", filed Jun. 3, 2014—3 pages.
European Patent No. EP1663182, Opposition document, "Claims for 1st Auxiliary Request", filed Jun. 3, 2014—4 pages.
European Patent No. EP1663182, Opposition document, "Claims for 2nd Auxiliary Request", filed Jun. 3, 2014—3 pages.
European Patent No. EP1663182, Opposition document, "Claims for 3rd Auxiliary Request", filed Jun. 3, 2014—4 pages.
European Patent No. EP1663182, Opposition document, "Claims for 4th Auxiliary Request", filed Jun. 3, 2014—3 pages.
European Patent No. EP1663182, Opposition document, "Claims for 5th Auxiliary Request", filed Jun. 3, 2014—2 pages.
European Patent No. EP1663182, Opposition document, "Claims for 6th Auxiliary Request", filed Jun. 3, 2014—2 pages.
European Patent No. EP1663182, Opposition document, "Claims for 1st Auxiliary Request" (Redlined Version), filed Jun. 3, 2014—4 pages.
European Patent No. EP1663182, Opposition document, "Claims for 2nd Auxiliary Request" (Redlined Version), filed Jun. 3, 2014—4 pages.
European Patent No. EP1663182, Opposition document, "Claims for 3rd Auxiliary Request" (Redlined Version), filed Jun. 3, 2014—4 pages.
European Patent No. EP1663182, Opposition document, "Claims for 4th Auxiliary Request" (Redlined Version), filed Jun. 3, 2014—4 pages.
European Patent No. EP1663182, Opposition document, "Claims for 5th Auxiliary Request" (Redlined Version), filed Jun. 3, 2014—3 pages.
European Patent No. EP1663182, Opposition document, "Claims for 6th Auxiliary Request" (Redlined Version), filed Jun. 3, 2014—4 pages.
European Patent No. EP1663182, Opposition document, Reply of the Patent Proprietor to the Notice of Opposition, dated May 28, 2014—17 pages.
European Patent No. EP1663182, Opposition document, Brief Communication Regarding Form 2548 and Amendment to Representation, dated Mar. 3, 2014—4 pages.
European Patent No. EP1663182, Opposition document, Brief Communication Regarding EPO Form 2944C of Mar. 31, 2014, dated Mar. 3, 2014—3 pages.
European Patent No. EP1663182, Opposition document, Grant of Extension of Time Limit, dated Mar. 31, 2014—1 page.
European Patent No. EP1663182, Opposition document, Invitation to File an Authorisation, dated Mar. 26, 2014, 1 page.
European Patent No. EP1663182, Opposition document, Letter Regarding Change of Representation, dated Mar. 21, 2014—1 page.
European Patent No. EP1663182, Opposition document, Request for Change of Applicant's Representative, dated Mar. 14, 2014—1 page.
European Patent No. EP1663182, Opposition document, Amended Data Concerning Representation, dated Mar. 21, 2014—1 page.
European Patent No. EP1663182, Opposition document, Communication of a Notice of Opposition and Request to File Other Observances, dated Nov. 20, 2013—1 page.
European Patent No. EP1663182, Opposition document, Communication of Further Notices of Opposition Pursuant to Rule 79(2) EPC, dated Nov. 20, 2013—3 pages.
International Preliminary Report on Patentability issued in the International Application No. PCT/US2004/026732, dated Mar. 13, 2006 (8 pages).
The Pharmaceutical Codex: Principles and Practice of Pharmaceutices (12th Ed.) (1994) pp. 178-197.
Kibbe, Arthur H., "Handbook of Pharmaceutical Excipients" (3rd Ed.) (2000) pp. 102-105, 143-145, 162-163, 305-308, 433-439, 522-527.
Ansel, Howard C., et al. "Pharmaceutical Dosage Forms and Drug Delivery Systems" (7th Ed.) (1999), pp. 87-92, 179-228.

(56) References Cited

OTHER PUBLICATIONS

Lieberman Herbert, Al, et al. "Pharmaceutical Dosage Forms: Tablets" (2nd Ed.) (1989) vol. 1, pp. 5-9, 75-130, 229-244.
Lieberman Herbert, Al, et al. "Pharmaceutical Dosage Forms: Tablets" (2nd Ed.) (1989) vol. 2, pp. 174-178, Figure 53.
"New Agent Reduces PTH Levels in Hemodialysis Patients with Secondary Hyperparathyroidism" Formulary (Apr. 2003) vol. 38, p. 197.
Chaumeil, J.C., "Micronization: A Method of Improving the Bioavailability of Poorly Soluble Drugs", Meth. Find. Exp. Clin. Pharmacol. (1998) pp. 211-215.
Dollery, Sir Colin "Therapeutic Drugs" (1991) vol. 2, pp. S85.
McInnes, Gordon T., et al. "Effect of Micronization on the Bioavailability and Pharmacologic Activity of Spironolactone", J. Clin. Pharmacol. 22 (1982), pp. 410-417.
"Orange Book: Approved Drug Products with Therapeutic Equivalence Evaluations", Patent and Exclusivity Search Results from query on Appln. No. 021688 Product 001 in OB_RX list: http://www.accessdata.fda.gov/scripts/cder/ob/docs/patexclnew.cfm?Appl_No=021688&Product_No=001&table1=OB_Rx.
Armando, Negri et al., "Agentes calciomimeticos en el traramiento del hiperparatirodidismo securdario a la insuficiencia renal cronica" Medicina (Buenos Aires) 2003; 63 pp. 165-171.
Ritschel Wolfgang: "Der Pharmazeutische Betrieb" Jan. 1, 2002, Editio Cantor Verlag, Aulendorf vol. 7, pp. 68-89, 122-127.
Frazao, Joao M., et al., "The calcimimetic agents: Perspectives for treatment", Kidney International, vol. 61, Supp. 80, 2002, pp. S149-S154.
Jounela, A.J., et al., "Effect of Particle Size on the Bioavailability of Digoxin", Eur. J. Clin. Pharmacol., vol. 8 No. 5, 1975, pp. 365-370.
Ridolfo, AS et al., "Benoxaprofen, a New Anti-Inflammatory Agent: Particle-Size Effect on Dissolution Rate and Oral Absorption in Humans". J. Pharm. Sci., vol. 68 No. 7 (1979) pp. 850-852.
Particle Size—U.S. Sieve Series and Tyler Mesh Series Equivalents (2002; updated 2013), found at www.azom.com/article.aspx?ArticleID=1417, pp. 1-2.
Petition for Inter Partes Review of U.S. Pat. No. 7,829,595, dated Oct. 26, 2015.
Declaration of Walter G. Chambliss, Ph.D., dated Aug. 18, 2015.
Akizawa, Tadao et al., "Management of secondary hyperparathyroidism of dialysis patients", Nephrology 2003, 8, pp. S53-S57.
IPR 2015-00562 (Exhibit 1022).
A.R. Gennaro, "Remington: The Science and Practice of Pharmacy", Ed. by Lippincott Williams & Wilkins, 20th ed., published Dec. 15, 2000, pp. 848-857.
"Handbook of Pharmaceutical Excipients", 1st ed., 1986, p. 239.
"Handbook of Pharmaceutical Excipients", 4th ed., edited by Raymond C. Rowe, Paul J. Shesky & Paul J. Weller, p. 161.
Howard C. Ansel et al., Pharmaceutical Dosage Forms and Drug Delivery Systems, (7th ed. 1999), pp. 109-110.
Decision Denying Institution for Inter Partes Review of U.S. Pat. No. 7,829,595, Case IPR2016-00085, entered Apr. 13, 2016.
Petitioners Request for Rehearing of Decision Denying Institution for Inter Partes Review of U.S. Pat. No. 7,829,595, Case IPR2016-00085, filed May 13, 2016.

* cited by examiner

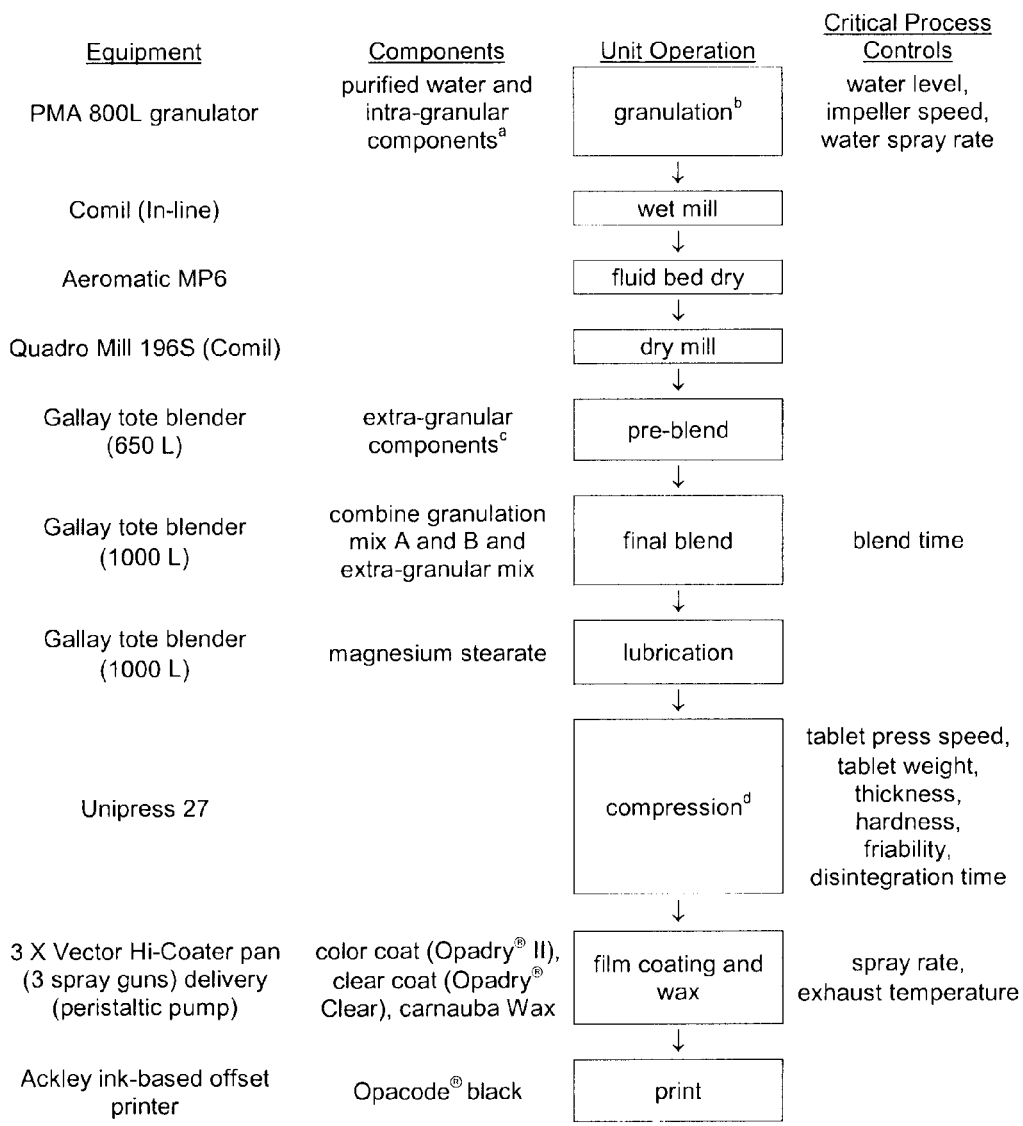

| Equipment | Components | Unit Operation | Critical Process Controls |
|---|---|---|---|
| PMA 800L granulator | purified water and intra-granular components[a] | granulation[b] | water level, impeller speed, water spray rate |
| Comil (In-line) | | wet mill | |
| Aeromatic MP6 | | fluid bed dry | |
| Quadro Mill 196S (Comil) | | dry mill | |
| Gallay tote blender (650 L) | extra-granular components[c] | pre-blend | |
| Gallay tote blender (1000 L) | combine granulation mix A and B and extra-granular mix | final blend | blend time |
| Gallay tote blender (1000 L) | magnesium stearate | lubrication | |
| Unipress 27 | | compression[d] | tablet press speed, tablet weight, thickness, hardness, friability, disintegration time |
| 3 X Vector Hi-Coater pan (3 spray guns) delivery (peristaltic pump) | color coat (Opadry® II), clear coat (Opadry® Clear), carnauba Wax | film coating and wax | spray rate, exhaust temperature |
| Ackley ink-based offset printer | Opacode® black | print | |

[a] cinacalcet HCl, pregelatinized starch, microcrystalline cellulose, povidone, and crospovidone
[b] The granulation step to dry milling step is repeated to generate 2 bowls of wet granulation (Mix A and B).
[c] Extra-granular components are microcrystalline cellulose, crospovidone, and colloidal silicon dioxide
[d] Tooling dimension is dependent on tablet size and strength, (30 mg; 0.2372" x 0.3800" oval shape plain, 60 mg; 0.3000" x 0.4800" modified oval (double radius) plain, 90 mg; 0.3420" x 0.5480" modified oval (double radius) plain)

RAPID DISSOLUTION FORMULATION OF A CALCIUM RECEPTOR-ACTIVE COMPOUND

This application claims the benefit of priority of U.S. Provisional Patent Application No. 60/502,219, filed Sep. 12, 2003.

Calcium receptor-active compounds are known in the art. One example of a calcium receptor-active compound is cinacalcet HCl, which is described, for example, in U.S. Pat. No. 6,001,884. Such calcium receptor-active compounds may be insoluble or sparingly soluble in water, particularly in their non-ionized state. For example, cinacalcet has a solubility in water of less than about 1 μg/mL at neutral pH. The solubility of cinacalcet can reach about 1.6 mg/mL when the pH ranges from about 3 to about 5. However, when the pH is about 1, the solubility decreases to about 0.1 mg/mL. Such limited solubility can reduce the number of formulation and delivery options available for these calcium receptor-active compounds. Limited water solubility can also result in low bioavailability of the compounds.

There is therefore a need to maximize the dissolution of the calcium receptor-active compound from a dosage form, and potentially during in vivo exposure. There is also a need to improve the bioavailability of the calcium receptor-active compound during in vivo exposure.

One aspect of the present invention provides a pharmaceutical composition comprising at least one calcium receptor active compound in combination with at least one pharmaceutically acceptable carrier. Certain embodiments of the present invention are directed to a pharmaceutical composition with a defined dissolution profile.

The invention also provides a method of manufacturing the pharmaceutical composition to achieve the desired dissolution profile, as well as a method of treating a disease using the pharmaceutical composition. In addition, certain embodiments of the present invention are directed to a method for controlling dissolution rate of a formulation comprising the pharmaceutical composition.

According to one aspect of the invention, the invention provides a pharmaceutical composition comprising an effective dosage amount of at least one calcium receptor-active compound and at least one pharmaceutically acceptable excipient, wherein the composition has a dissolution profile in 0.05 N HCl, measured according to a dissolution test conducted in United States Pharmacopeia (USP)—National Formulary (NF) (USP 26/NF 21), chapter 711 using a USP 2 apparatus at a temperature of 37° C.±0.5° C., and at a rotation speed of 75 r.p.m., which comprises from about 50% to about 125% of a target amount of the calcium receptor-active compound being released from the composition no later than about 30 minutes from the start of the test.

According to another aspect of the invention, the invention provides a pharmaceutical composition comprising an effective dosage amount of at least one calcium receptor-active compound and at least one pharmaceutically acceptable excipient, wherein the composition has a dissolution profile in 0.05 N HCl, measured according to a dissolution test conducted in USP 26/NF 21, chapter 711 using a USP 2 apparatus at a temperature of about 37° C., and at a rotation speed of about 75 r.p.m., which comprises from about 50% to about 125% of a target amount of the calcium receptor-active compound being released from the composition no later than about 30 minutes from the start of the test.

The invention also provides a method of controlling the dissolution rate of a formulation comprising an effective dosage amount of a calcium receptor-active compound and at least one pharmaceutically acceptable excipient, the method comprising producing the formulation in a granulator which has a volume ranging from about 1 L to about 2000 L, and contains water in a granulation level ranging from about 10% to about 50% relative to the weight of the dry powders in the granulator.

The calcium receptor-active compound useful in the claimed invention may be a calcimimetic compound or a calcilytic compound. As used herein, the term "calcimimetic compounds" refers to compounds that bind to a calcium receptor, and induce a conformational change that reduces the threshold for calcium receptor activation by the endogenous ligand $Ca^{2+}$, thereby reducing parathyroid hormone ("PTH") secretion. These calcimimetic compounds can also be considered allosteric modulators of the calcium receptor. As used herein, the term "calcilytic compounds" refers to compounds that act as calcium receptor antagonists, and stimulate PTH secretion.

The calcimimetic compounds and calcilytic compounds useful in the present invention include those disclosed in, for example, European Patent No. 933 354; International Publication Nos. WO 01/34562, WO 93/04373, WO 94/18959, WO 95/11221, WO 96/12697, WO 97/41090; U.S. Pat. Nos. 5,981,599, 6,001,884, 6,011,068, 6,031,003, 6,172,091, 6,211,244, 6,313,146, 6,342,532, 6,363,231, 6,432,656, and U.S. Patent Application Publication No. 2002/0107406. The calcimimetic compounds and/or calcilytic compounds disclosed in these patents and published applications are incorporated herein by reference.

In certain embodiments, the calcium receptor-active compounds are chosen from compounds of formula (I) and pharmaceutically acceptable salts thereof

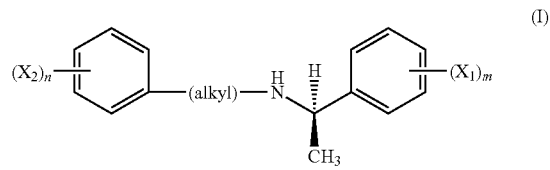

(I)

wherein:

$X_1$ and $X_2$, which may be identical or different, are each a radical chosen from $CH_3$, $CH_3O$, $CH_3CH_2O$, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, and acetyl radicals, or two of $X_1$ may together form an entity chosen from fused cycloaliphatic rings, fused aromatic rings, and a methylene dioxy radical, or two of $X_2$ may together form an entity chosen from fused cycloaliphatic rings, fused aromatic rings, and a methylene dioxy radical; provided that $X_2$ is not a 3-t-butyl radical;

n ranges from 0 to 5;

m ranges from 1 to 5; and the alkyl radical is chosen from C1-C3 alkyl radicals, which are optionally substituted with at least one group chosen from saturated and unsaturated, linear, branched, and cyclic C1-C9 alkyl groups, dihydroindolyl and thiodihydroindolyl groups, and 2-, 3-, and 4-piperid(in)yl groups; and the stereoisomers thereof.

Calcium receptor-active compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methanesulfonate, nicotinate, 2-naphthalene-sulfonate, oxalate, palmoate, pectinate, persulfate, 2-phenyl-propionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al., *J. Pharm. Sci.* 66:1 (1977). In certain embodiments of the invention salts of hydrochloride and salts of methanesulfonic acid can be used.

In some embodiments of the present invention, the calcium-receptor active compound can be chosen from cinacalcet, i.e., N-(1-(R)-(1-naphthyl)ethyl]-3-[3-(trifluoromethyl) phenyl]-1-aminopropane, cinacalcet HCl, and cinacalcet methanesulfonate. The cinacalcet HCl and cinacalcet methanesulfonate can be in various forms, such as amorphous powders, crystalline powders, and mixtures thereof. For example, the crystalline powders can be in forms including polymorphs, psuedopolymorphs, crystal habits, micromeretics, and particle morphology.

The therapeutically effective amount of the calcium receptor-active compound in the compositions disclosed herein ranges from about 1 mg to about 360 mg, for example from about 5 mg to about 240 mg, or from about 20 mg to about 100 mg. As used herein, the "therapeutically effective amount" is an amount that changes in a desired manner at least one of the calcium level, the phosphorus level, the PTH level, and the calcium phosphorus product in a subject. In some embodiments, the therapeutically effective amount of cinacalcet HCl in the composition disclosed herein can be chosen from about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg.

While it may be possible to administer a compound of the invention alone, the compound administered will normally be present as an active ingredient in a pharmaceutical composition. Thus, a pharmaceutical composition of the invention may comprise a therapeutically effective amount of at least one calcium receptor-active compound, or an effective dosage amount of at least one calcium receptor-active compound.

As used herein, an "effective dosage amount" is an amount that provides a therapeutically effective amount of the at least one calcium receptor active compound when provided as a single dose, in multiple doses, or as a partial dose. Thus, an effective dosage amount of the at least one calcium receptor active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the at least one calcium receptor-active compound is administered by administering a portion of the composition.

Alternatively, a pharmaceutical composition in which two or more unit dosages, such as in tablets, capsules and the like, are required to administer an effective amount of the at least one calcium receptor active compound may be administered in less than an effective amount for one or more periods of time (i.e., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition disclosed herein ranges from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

In some embodiments of the present invention, the compositions disclosed herein comprise a therapeutically effective amount of cinacalcet HCl for the treatment of hyperparathyroidism, such as primary hyperparathyroidism and secondary hyperparathyroidism, hyperphosphonia, hypercalcemia, and elevated calcium-phosphorus product. For example, in certain embodiments, the cinacalcet HCl can be present in an amount ranging from about 1% to about 70%, such as from about 5% to about 40%, from about 10% to about 30%, or from about 15% to about 20%, by weight relative to the total weight of the composition.

The compositions of the invention may contain one or more active ingredients in addition to the calcium receptor-active compound. The additional active ingredient may be another calcium receptor-active compound, or it may be an active ingredient having a different therapeutic activity. Examples of such additional active ingredients include, for example, vitamins and their analogs, such as vitamin D and analogs thereof, antibiotics, and cardiovascular agents.

The cinacalcet HCl or other calcium receptor-active compound that can be used in the composition is typically present in the form of particles. These particles can have a particle $D_{50}$ of, for example, less than or equal to about 50 µm. As used herein, the "particle $D_{50}$" is the particle size of the active pharmaceutical ingredient at the $50^{th}$ percentile of a particle size distribution. According to certain embodiments of the invention, the active pharmaceutical ingredient in the formulation has a particle $D_{50}$ that is less than the granule $D_{50}$ of the formulation, discussed in detail below.

The particle $D_{50}$ of the cinacalcet HCl particles can be determined by one of ordinary skill in the art using known light scattering techniques. In one embodiment of the invention, the particle $D_{50}$ of the cinacalcet HCl particles is determined by using a particle size analyzer, such as a Malvern Mastersizer analyzer, that uses a laser to scan a suspension of particles. The particles diffract the incoming light to detectors: smaller particles diffract light at larger angles, while larger particles diffract light at smaller angles. The light intensities observed at each detector are translated into a particle size distribution based on the diameter of a sphere that has an equivalent volume to that of the measured particles.

Specifically, the particle size distribution of the active pharmaceutical ingredient, for example, cinacalcet HCl, can be determined according to the following procedure. The following instrument conditions in a Malvern Mastersizer particle size analyzer are specified in its software:

| | |
|---|---|
| Refractive Index Sample | 1.630 |
| Absorptive Index | 0.1 |
| Refractive Index Dispersant | 1.375 |
| Analysis model | General purpose spherical |
| Calculation sensitivity | Enhanced |

-continued

| | |
|---|---|
| Measurement snaps and time | 20,000 snaps over 20 seconds |
| Background snaps and time | 20,000 snaps over 20 seconds |
| Stir speed | 1750 rpm |

While stirring, about 170 mL of a dispersion of about 0.1% sorbitan trioleate (for example Span 85®, available from Kishida Chemical) in hexane ("dispersant-B"), is added to the sampling unit, and the laser is aligned to take a background measurement of the dispersant-B.

The entire suspension containing the cinacalcet HCl is added until a suitable obscuration range ranging from about 10 to about 20% is obtained. The sample is measured after the obscuration value has stabilized. After the measurement, the system is drained and rinsed once with about 170 mL of dispersant-B, the dispersant-B is drained, and the sampling unit is refilled with about 170 mL of dispersant-B. The measurement are repeated two more times with different riffled fractions. The riffling is performed on large samples to obtain small representative particle size fractions about 15 mg in size.

The Obscuration, D(v,0.1), D(v,0.5), D(v,0.9) values are then calculated from these measurements. The average, standard deviation, and relative standard deviation (RSD) of the D(v,0.1), D(v,0.5), D(v,0.9) values is also calculated. The RSD (%) is calculated as follows:

$$RSD\ (\%) = \frac{100}{\overline{X}} \left[ \frac{\sum_{i=1}^{N} (X_i - \overline{X})^2}{N-1} \right]^{\frac{1}{2}}$$

where $X_i$ is an individual measurement in a set of N measurements and is the arithmetic mean of the set.

The composition disclosed herein can be in various forms, for example, in granular form. The granules that can be used in the present invention can have a granule $D_{50}$ ranging from about 50 µm to about 150 µm, such as from about 80 µm to about 130 µm. As defined herein, the "granule $D_{50}$" is the particle size of the composition at the $50^{th}$ percentile of a particle size distribution. The granule $D_{50}$ can readily be determined by one of ordinary skill in the art using sieve analysis techniques. Specifically, the granule $D_{50}$ is determined according to the following procedure.

Approximately 100 g of sample is added to sieve shaker equipped with 40 mesh, 60 mesh, 80 mesh, 100 mesh, 140 mesh, 200 mesh, 325 mesh, and the bottom pan. The sieve shaker is then turned on for about 10 minutes to separate the sample according to particle size. Each sieve is weighed to determine the amount of sample retained on each sieve and the bottom pan. The individual sieve weight is normalized to generate sieve weight fraction. The individual sieve weight fraction is calculated by dividing each sieve weight with the sum of all sieve weights.

$$\text{Weight Fraction of each sieve} = \frac{\text{Weight of each sieve}}{\text{Sum of all sieves}}$$

Before the particle size calculation, the mean size range must be determined for each sieve and the bottom pan. This mean size of each sieve screen represents the mean particle size retained on the screen. The mean size of each sieve screen is determined by the hole size of the screen (lower limit) and one sieve size larger (upper limit). In the case of the 40 mesh sieve screen, the hole size of about 1410 µm is used as an upper limit. Table 1 set forth below shows the particle size range of any retained material on each screen and the mean of the particle size range.

TABLE 1

| Screens | Hole size of each screen (µm) | Particle size range of retained material on each screen (µm) | Median particle size of the screen (µm) |
|---|---|---|---|
| 40 mesh | 425 | 425-1410 | 918 |
| 60 mesh | 250 | 250-424 | 337 |
| 80 mesh | 180 | 180-249 | 215 |
| 100 mesh | 150 | 150-179 | 165 |
| 140 mesh | 106 | 106-149 | 128 |
| 200 mesh | 75 | 75-105 | 90 |
| 325 mesh | 45 | 45-74 | 60 |
| Bottom pan | 0 | 1-44 | 23 |

The weight fraction of each sieve is added to generate cumulative frequency distribution starting from the bottom pan to 40 mesh screen. Once the cumulative frequency distribution is generated, the corresponding particle size at 10 percentile ($D_{10}$), 50-percentile ($D_{50}$), and 90-percentile ($D_{90}$) are determined. The particle size of the corresponding percentile is determined by linear interpolation between two consecutive data from the cumulative frequency distribution. For example, particle size of 50-percentile ($D_{50}$) is interpolated by, $$D_{50}(\mu m) = \frac{[(50 - X_n) * d_{n+1} + (X_{n+1} - 50) * d_n]}{(X_{n+1} - X_n)}$$

where, $X_n$=cumulative quantity of sample that is just below 50-percentile (in %);

$d_n$=mean of the particle size range from the sieve screen where $X_n$ occurs (in mm);

$X_{n+1}$=next cumulative quantity of sample that is above 50-percentile (in %).

$d_{n+1}$=mean of the particle size range from the sieve screen where $X_{n+1}$ occurs (in mm).

According to all embodiments of the present invention, the particle size of active pharmaceutical ingredient is measured according to light scattering techniques, and the particle size of the granules of composition is measured according to sieve analysis.

The compositions disclosed herein can be in a form chosen from, for example, tablets, capsules, and powders. The tablets can be made by pressing the granules into the form of tablets. The capsules can also be made using the granules.

The at least one pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxyl methylcellulose; and disintegrants such as crospovidone, sodium starch glycolate, croscarmellose sodium, and mixtures of any of the foregoing. The at least one pharmaceutically acceptable excipient can further be chosen from lubricants such as magnesium stearate, calcium stearate, stearic acid, glyceryl behenate, hygrogenated vegetable oil, glycerine fumarate and glidants such as colloidal silicon dioxide, and mixtures thereof. In some embodiments of the present invention, the at least one pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients of the present invention, can be intragranular, intergranular, or mixtures thereof.

In some embodiments of the present invention, the composition and/or the granules within the composition can comprise microcrystalline cellulose and starch in a weight ratio ranging from about 1:1 to about 15:1. For example, in the composition, the weight ratio of the microcrystalline cellulose and starch can range from about 1:1 to about 15:1, such as about 10:1, and in the granules within the composition, the weight ratio of the microcrystalline cellulose and starch can range from about 1:1 to about 10:1, such as about 5:1.

The microcrystalline cellulose can be present in an amount ranging from about 25% to about 85%, for example from about 50% to about 80%, or from about 60% to about 75% by weight relative to the total weight of the composition. The starch can be present in an amount ranging from about 5% to about 35%, for example, from about 5% to about 25%, or from about 5% to about 10% by weight relative to the total weight of the composition.

The compositions disclosed herein can further comprise at least one ingredient chosen from coating materials that are known in the art such as, for example, hydroxypropyl methylcellulose.

Certain compositions can comprise:

(a) from about 10% to about 40% by weight of a calcium receptor-active compound chosen from cinacalcet HCl and cinacalcet methanesulfonate;

(b) from about 45% to about 85% by weight of at least one diluent;

(c) from about 1% to about 5% by weight of at least one binder; and (d) from about 1% to about 10% by weight of at least one disintegrant;

wherein the percentage by weight is relative to the total weight of the composition. The compositions can further comprise from about 0.05% to about 5% by weight, relative to the total weight of the composition, of at least one additive chosen from glidants, lubricants, and adherents. The composition can additionally comprise from about 1% to about 6% by weight of at least one coating material, relative to the total weight of the composition.

In another embodiment, the composition disclosed herein comprises:

(a) from about 10% to about 40% by weight of cinacalcet HCl;

(b) from about 5% to about 10% by weight of starch;

(c) from about 40% to about 75% by weight of microcrystalline cellulose;

(d) from about 1% to about 5% by weight of povidone; and (e) from about 1% to about 10% by weight of crospovidone;

wherein the percentage by weight is relative to the total weight of the composition.

The povidone can be present in an amount ranging from about 1% to about 5%, for example, from about 1% to about 3% by weight relative to the total weight of the composition. The crospovidone can be present in an amount ranging from about 1% to about 10%, for example from about 3% to about 6%, by weight relative to the total weight of the composition.

The composition can further comprise from about 0.05% to about 5% by weight, relative to the total weight of the composition, of at least one additive chosen from colloidal silicon dioxide, magnesium stearate, talc, and the like, and mixtures of any of the foregoing. In certain embodiments of the invention, the composition comprises from about 0.05% to about 1.5% of colloidal silicon dioxide, from about 0.05% to about 1.5% of magnesium stearate, from about 0.05% to about 1.5% of talc, or mixtures of any of the foregoing. The composition can even further comprise from about 1% to about 6% by weight of at least one coating material, relative to the total weight of the composition.

As mentioned above, the compositions of certain embodiments of the present invention have a dissolution profile that results in about 50% to about 125% of a target amount of the calcium receptor-active compound being released from the composition no later that about 30 minutes from the start of a dissolution test that is conducted in 0.05 N HCl in a U.S.P. 2 apparatus at a temperature of 37° C.±0.5° C. at a rotation speed of 75 r.p.m. The dissolution test is conducted using a USP 2 apparatus, and according to the dissolution protocol described in USP 26/NF 21, chapter 711, which is incorporated herein by reference. According to this embodiment using this dissolution protocol, a stated volume of the dissolution medium (±1%) is placed in the vessel of the USP 2 apparatus, the apparatus is assembled, the dissolution medium is equilibrated to 37° C.±0.5° C., the thermometer is removed, the dosage form is placed in the vessel, and the amount of active pharmaceutical ingredient that is released as a function of time is measured.

According to another embodiment of the invention, a stated volume of the dissolution medium is placed in the vessel of the USP 2 apparatus, the apparatus is assembled, the dissolution medium is equilibrated to about 37° C., the thermometer is removed, the dosage form is placed in the vessel, and the amount of active pharmaceutical ingredient that is released as a function of time is measured.

The dissolution profile represents the percentage of the active pharmaceutical ingredient released based on a target amount of the active pharmaceutical ingredient in the formulation. As used herein "target amount" refers to the amount of active pharmaceutical ingredient in each formulation. In certain embodiments, the target amount refers to the label amount and/or label claim.

USP 26/NF 21, chapter 905, defines a protocol used to determine the dosage-unit conformity according to the present invention, and this content uniformity protocol is incorporated herein by reference. According to this protocol, the content uniformity is determined by measuring the amount of active pharmaceutical ingredient in 10 dosage unit samples, and calculating whether the amount of active pharmaceutical ingredient in all the dosage unit samples falls within a range of 85% to 115% of the target amount. If one dosage unit sample is outside the range of 85% to 115% of the target amount and no unit is outside a range of 75% to 125% of the target amount, or if the Relative Standard Deviation (RSD), which is the sample standard deviation expressed as a percentage of the mean, is not greater than 6%, then 20 additional dosage unit samples are tested. After treating at least 30 dosage units, the content uniformity requirement is met if not more than one dosage unit sample is outside the range of 85% to 115% of the target amount, and no unit is outside a range of 75% to 125% of the target amount, and the RSD of the at least 30 dosage units does not exceed 7.8%.

In certain embodiments, the dissolution profile of the compositions disclosed herein can result in, for example, at least about 50%, at least about 70%, at least about 75%, or at least about 85%, of the target amount of the calcium receptor-active compound being released from the composition no later than about 30 minutes from the start of the test. In certain embodiments, the dissolution profile of the compositions disclosed herein can comprise at most about 125%, for example at most about 115%, at most about 110%, or at most about 100% of the target amount of the calcium receptor-active compound being released from the composition no later than about 30 minutes from the start of the test. In additional embodiments, the dissolution profile of the compositions disclosed herein can comprise from about 50% to about 125%, for example from about 70% to about 110%, of the target amount of the calcium receptor-active compound being released from the composition no later than about 30 minutes from the start of the test.

Other embodiments of the present invention are directed to a method of making a pharmaceutical composition comprising:

(a) forming a granule comprising a calcium receptor-active compound and at least one pharmaceutically acceptable excipient as disclosed herein; and (b) controlling the particle size of the granule such that from about 50% to about 125% of a target amount of calcium receptor-active compound is released from the composition no later than about 30 minutes from the start of a test in 0.05 N HCl according to a dissolution test conducted in a USP 2 apparatus at a temperature of 37° C.±0.5° C., and a rotation speed of 75 r.p.m.

Further embodiments of the present invention are directed to a method of making a pharmaceutical composition comprising:

(b) forming a granule comprising a calcium receptor-active compound and at least one pharmaceutically acceptable excipient as disclosed herein; and (b) controlling the particle size of the granule such that from about 50% to about 125% of a target amount of calcium receptor-active compound is released from the composition no later than about 30 minutes from the start of a test in 0.05 N HCl according to a dissolution test conducted in a USP 2 apparatus at a temperature of about 37° C., and a rotation speed of about 75 r.p.m.

The granule can be formed by any known process, such as high wet shear granulation, low wet shear granulation, fluid bed granulation, rotary granulation, extrusion-spheronization, dry granulation, roller compaction, and the like.

The particle size of the granule of the composition can be controlled by various factors. In certain embodiments of the present invention, the particle size of the granule of the composition can be controlled by the amount of water added to the materials present in a granulator. For example, a desired particle size of the granule can be achieved when the granulator has a volume ranging from about 1 L to about 1200 L, such as from about 65 L to about 1200 L, or from about 300 L to about 800 L, and the amount of water added ranges from about 20% to about 40%, such as from about 30% to about 36%, relative to the amount of dry powders present in the granulator to form the granules.

The granulator's impeller tip speed can also affect the particle size of the granules. In some embodiments, the impeller tip speed, measured in meters per second (m/s), can range from about 5 m/s to about 10 m/s, such as from about 7 m/s to about 9 m/s.

Other embodiments of the present invention are directed to a method of making a pharmaceutical composition comprising (a) forming a composition comprising a therapeutically effective amount of particles of a calcium receptor-active compound and at least one pharmaceutically acceptable excipient as disclosed herein; and (b) controlling the particle size of the calcium receptor-active compound such that from about 50% to about 125% of a target amount of the calcium receptor-active compound is released from the composition no later than about 30 minutes from the start of a test in 0.05 N HCl according to a dissolution test conducted in a USP 2 apparatus at a temperature of 37° C.±0.5° C., and a rotation speed of 75 r.p.m.

Additional embodiments of the present invention are directed to a method of making a pharmaceutical composition comprising (a) forming a composition comprising a therapeutically effective amount of particles of a calcium receptor-active compound and at least one pharmaceutically acceptable excipient as disclosed herein; and (b) controlling the particle size of the calcium receptor-active compound such that from about 50% to about 125% of a target amount of the calcium receptor-active compound is released from the composition no later than about 30 minutes from the start of a test in 0.05 N HCl according to a dissolution test conducted in a USP 2 apparatus at a temperature of about 37° C., and a rotation speed of about 75 r.p.m.

The size of the particles is controlled during the production of the active pharmaceutical ingredient, for example, by use of a milling step, or a controlled crystallization process. For example, the active pharmaceutical ingredient can be milled using a stainless steel hammer mill with 5 mm screen and 12 hammers forward at a mill speed of 8100±100 rpm, with the feed speed is set at 90±10 rpm.

Yet other embodiments of the present invention are directed to a method for the treatment of a disease or disorder that can be treated by altering a subject's calcium receptor activity. In some embodiments, a method for the treatment of a disease chosen from hyperparathyroidism, such as primary hyperparathyroidism and secondary hyperparathyroidism, hyperphosphonia, hypercalcemia, and elevated calcium-phosphorus product comprises administering to a patient, such as human, an effective dosage amount of a pharmaceutical composition comprising a calcium receptor-active compound and at least one pharmaceutically acceptable excipient as disclosed herein, wherein the composition has a dissolution profile in 0.05 N HCl, measured according to a dissolution test conducted in a USP 2 apparatus at a temperature of 37° C.±0.5° C., and at a rotation speed of 75 r.p.m., which comprises from about 50% to about 125% of a target amount of the calcium receptor-active compound being released from the composition in no later than about 30 minutes from the start of the test.

A further embodiment of the present invention is directed to a method for the treatment of a disease chosen from hyperparathyroidism, hyperphosphonia, hypercalcemia, and elevated calcium-phosphorus product comprises administering to a patient, such as human, an effective dosage amount of a pharmaceutical composition comprising a calcium receptor-active compound and at least one pharmaceutically acceptable excipient as disclosed herein, wherein the composition has a dissolution profile in 0.05 N HCl, measured according to a dissolution test conducted in a USP 2 apparatus at a temperature of about 37° C., and at a rotation speed of about 75 r.p.m., which comprises from about 50% to about 125% of a target amount of the calcium receptor-active compound being released from the composition in no later than about 30 minutes from the start of the test.

Reference will now be made to the following examples which are not intended to limit the invention. To the contrary, it will be appreciated that various alternatives, modifications, and equivalents may be included within the spirit and scope of the invention.

BRIEF DESCRIPTION OF THE DRAWINGS

FIG. 1: A process Flow diagram showing a process by which 30-, 60- and 90-mg tablets of active pharmaceutical ingredient are prepared.

EXAMPLES

Three pharmaceutical formulations with target amounts of 30 mg, 60 mg, and 90 mg active pharmaceutical ingredient with the following components were prepared:

|  | Weight % (w/w) | 30 mg Tablet Amount (mg) | 60 mg Tablet Amount (mg) | 90 mg Tablet Amount (mg) |
|---|---|---|---|---|
| Cinacalcet HCl | 18.367 | 33.06 | 66.12 | 99.18 |
| Pregelatinized starch (Starch 1500) | 33.378 | 60.08 | 120.16 | 180.24 |
| Microcrystalline cellulose (Avicel PH102) | 6.678 | 12.02 | 24.04 | 36.06 |
| Povidone (Plasdone K29/32) | 2.044 | 3.68 | 7.36 | 11.04 |
| Crospovidone (Polyplasdone XL) | 1.233 | 2.22 | 4.44 | 6.66 |
| Purified Water[1] | — | — | — | — |
| Microcrystalline cellulose (Avicel PH102) | 34.300 | 61.74 | 123.48 | 185.22 |
| Magnesium stearate | 0.500 | 0.90 | 1.80 | 2.70 |
| Colloidal silicon dioxide (Colloidal anhydrous silica) (Cab-O-Sil M5P) | 0.500 | 0.90 | 1.80 | 2.70 |
| Crospovidone (Polyplasdone XL) | 3.000 | 5.40 | 10.80 | 16.20 |
| Core Tablet | 100.000 | 180.00 | 360.00 | 540.00 |
| Purified Water[1] | — | — | — | — |
| Opadry ® II (colored film former) | 4.000 | 7.20 | 14.40 | 21.60 |
| Purified Water[1] | — | — | — | — |
| Opadry ® Clear (clear film former) | 1.500 | 2.70 | 5.40 | 8.10 |
| Carnauba Wax Powder | 0.010 | 0.018 | 0.036 | 0.054 |
| Opacode ® Ink (Black)[2] | — | — | — | — |

[1]The purified Water was removed during processing.
[2]Trace quantities of ink were applied to the coated tablet.

The wet granulation process was conducted in a PMA 800 L high-shear granulator with water serving as the granulation fluid. The cinacalcet HCl and the intra-granulation excipients (pregelatinized starch, microcrystalline cellulose, povidone, and crospovidone) were dry-mixed for 1 to 2 minutes with an impeller speed set point at 116±10 rpm, followed by granulation with 30.0% to 36.0% w/w water (based on intra-granular lot size; target was 34.9% w/w) with an impeller speed set point at 116±10 rpm and at a slow or fast chopper speed (target was slow speed). During the granulation process water was delivered at 9.8±0.5 kg/min.

Following granulation, the mixture was wet-milled using an in-line Comil equipped with a 0.375" (0.953 cm) opening screen and an impeller speed set point at 1400±50 rpm. The mixture was then discharged into a fluid-bed dryer.

After completion of the wet-milling process, the granulation mixture was dried in an Aeromatic MP6 fluid bed dryer with an inlet temperature set point at 70°±5° C. When the outlet temperature reached 37° C. to 41° C., samples were taken to determine moisture levels by loss on drying (LOD). The granules were dried until the average moisture levels reached 1.0% to 2.5%.

The dried granulation mixture was milled through a Quadro Mill 196S (Comil) equipped with a 0.055" (0.140 cm) opening screen at an impeller speed of 1650±50 rpm into a 1000 L Gallay tote.

Except for magnesium stearate, the extra-granular excipients were blended in a 650 L Gallay tote blender for 7±1 minutes at 12±1 rpm. This mixture was further blended with the dry-milled granulation in a 1000 L Gallay tote blender for 15±5 minutes at 12±1 rpm, and then for 6±1 minutes at 12±1 rpm after magnesium stearate was added for lubrication.

The final lubricated blend was compressed into tablets containing 30-, 60-, or 90 mg of the free base equivalent of active cinacalcet HCl using a Unipress 27 tablet press set to a speed of 2000±300 tablets per minute and equipped with a force feeder. Throughout the compression operation, individual tablet weights (target weights of 180, 360, and 540 mg for 30-, 60-, and 90-mg tablets, respectively), the average weight of 10 tablets, tablet hardness and thickness were monitored at pre-determined intervals.

The color-coating suspension and clear-coating solution were prepared by slowly adding either the Opadry® II (green) or Opadry® Clear into purified water while mixing until uniform (≥45 minutes). The color suspension and clear solution deaerated for ≥45 minutes before the spraying process began, and were used within a pre-determined time limit.

Each lot was film-coated with color and clear coats in a Vector Hi-Coater 48" pan. The color-coating suspension was applied onto a moving core tablet bed (pan speed=4 to 7 rpm) and a spray rate of 250±50 grams per minute per 3 guns. The distance between the spray guns and the tablet bed was approximately 8" (20 cm) to 11" (28 cm), and the air volume was 600±200 ft$^3$ per minute (17.1±5.7 m$^3$ per minute) with a pan pressure differential maintained between −0.1" (−0.25 cm) to −0.3" (−0.76 cm) of water. Supply air temperature was adjusted to 80±10° C. to maintain an exhaust temperature of 41±3° C.

When the clear-coating application was completed, the heater and the air supply was turned off and the wax was spread evenly over the moving tablet bed (after it reached ≤37° C.) with a pan speed of 4 to 7 rpm. The tablets were rotated for 5±1 minutes, and after the supply air and exhaust fan were turned on, the tablets were rotated for an additional 5±1 minutes with a pan speed of 4 to 7 rpm and supply air of 600±200 ft$^3$ per minute (17.1±5.7 m$^3$ per minute). The pan was jogged until the tablet bed temperature reached ≤30° C.

An Ackley ink-based offset printer was used to produce 2-sided printed tablets.

The dissolution profile of the three formulations were measured according the dissolution protocol described in the USP 26/NF 21, chapter 711 using a USP 2 apparatus at a temperature of about 37° C., and at a rotation speed of about 75 r.p.m. The dissolution profile of the formulations in which at least about 75% of the cinacalcet HCl was released from the composition in no later than about 30 minutes from the start of the test is set forth in Table 2.

TABLE 2

| Time (min) | 30 mg Tablet | 60 mg Tablet | 90 mg Tablet |
|---|---|---|---|
| 15 | 85.3 | 81.9 | 80.8 |
| 30 | 95.2 | 93.8 | 93.4 |
| 45 | 97.7 | 97.7 | 97.9 |
| 60 | 98.7 | 98.8 | 99.8 |

The content uniformity of the three formulations were measured in accordance with USP 26/NF 21, chapter 905, described in detail above. The content uniformity and for each of the three formulations is set forth in Table 3.

TABLE 3

|           | 30 mg Tablet           |       | 60 mg Tablet           |       | 90 mg Tablet           |       |
|-----------|------------------------|-------|------------------------|-------|------------------------|-------|
| Container | Mean (10 tablets)      | % RSD | Mean (10 tablets)      | % RSD | Mean (10 tablets)      | % RSD |
| 1 (beg.)  | 98.5                   | 0.8   | 96.7                   | 1.6   | 99.7                   | 1.2   |
| 5         | 98.8                   | 0.8   | 98.5                   | 0.8   | 100.7                  | 0.9   |
| 11        | 98.5                   | 0.6   | 98.3                   | 1.0   | 99.9                   | 0.7   |
| 16        | 98.3                   | 0.8   | 97.6                   | 1.3   | 99.9                   | 0.5   |
| 22        | 98.3                   | 1.0   | 96.3                   | 1.8   | 100.7                  | 0.9   |
| end       | 98.0                   | 0.6   | 95.8                   | 1.9   | 99.3                   | 0.8   |

What is claimed is:

1. A pharmaceutical composition comprising:
   (a) from about 10% to about 40% by weight of cinacalcet HCl in an amount of from about 20 mg to about 100 mg;
   (b) from about 45% to about 85% by weight of a diluent selected from the group consisting of microcrystalline cellulose, starch, dicalcium phosphate, lactose, sorbitol, mannitol, sucrose, methyl dextrins, and mixtures thereof,
   (c) from about 1% to about 5% by weight of at least one binder selected from the group consisting of povidone, hydroxypropyl methylcellulose, hydroxypropyl cellulose, sodium carboxymethylcellulose, and mixtures thereof; and
   (d) from about 1% to 10% by weight of at least one disintegrant selected from the group consisting of crospovidone, sodium starch glycolate, croscarmellose sodium, and mixtures thereof,
   wherein the percentage by weight is relative to the total weight of the composition, and wherein the composition is for the treatment of at least one of hyperparathyroidism, hyperphosphonia, hypercalcemia, and elevated calcium phosphorus product.

2. The composition according to claim 1, further comprising at least one excipient selected from the group consisting of lubricants and clear and color coating materials.

3. The composition according to claim 1, further comprising from about 1% to about 6% by weight of at least one coating material selected from the group consisting of clear and color coating materials wherein the percentage by weight is relative to the total weight of the composition.

4. The composition according to claim 1, further comprising from about 0.05% to about 5% of at least one additive selected from the group consisting of glidants, lubricants and adherents, wherein the percentage by weight is relative to the total weight of the composition.

5. The composition according to claim 1, wherein the at least one binder is povidone.

6. The composition according to claim 1, wherein the at least one disintegrant is crospovidone.

7. The composition according to claim 6 wherein the form of the cinacalcet HCl is selected from the group consisting of needle-shape particles, rod-shape particles, plate-shaped particles, and mixtures thereof.

8. The composition according to claim 1, wherein the cinacalcet HCl is in a form selected from the group consisting of amorphous powders, crystalline particles, and mixtures thereof.

9. The composition according to claim 8 wherein the particle $D_{50}$ of the cinacalcet HCl particles is less than or equal to about 50 μm.

10. The composition according to claim 9, wherein the granules have a granule $D_{50}$ measured using a sieve analysis ranging from about 50 μm to about 150 μm.

11. The composition according to claim 9, wherein the granules have a granule $D_{50}$ measured using a sieve analysis ranging from about 80 μm to about 130 μm.

12. The composition according to claim 11, wherein the crospovidone is present intergranularly.

13. The composition according to claim 11, wherein the crospovidone is present intragranularly.

14. The composition according to claim 9, wherein the disintegrant is crospovidone and the crospovidone is present intergranularly, intragranularly, or a combination thereof.

15. The composition according to claim 1 wherein the composition comprises granules.

16. The composition according to claim 1 further comprising from about 0.05% to about 1.5% by weight of colloidal silicon dioxide relative to the total weight of the composition.

17. The composition according to claim 1 further comprising from about 0.05% to about 1.5% by weight of magnesium stearate relative to the total weight of the composition.

18. The composition according to claim 1, wherein the hyperparathyroidism is primary hyperparathyroidism or secondary hyperparathyroidism.

19. The composition according to claim 1, wherein the diluent is microcrystalline cellulose or starch.

20. A pharmaceutical composition comprising:
   (a) from about 10% to about 40% by weight of cinacalcet HCl in an amount of from about 20 mg to about 100 mg;
   (b) from about 45% to about 85% by weight of a diluent selected from the group consisting of microcrystalline cellulose, starch, dicalcium phosphate, lactose, sorbitol, mannitol, sucrose, methyl dextrins, and mixtures thereof,
   (c) from about 1% to about 5% by weight of at least one binder selected from the group consisting of povidone, hydroxypropyl methylcellulose, hydroxypropyl cellulose, sodium carboxymethylcellulose, and mixtures thereof; and
   (d) from about 1% to 10% by weight of at least one disintegrant selected from the group consisting of crospovidone, sodium starch glycolate, croscarmellose sodium, and mixtures thereof,
   wherein the disintegrant is at least present intragranularly and wherein the composition is for the treatment of at least one of hyperparathyroidism, hyperphosphonia, hypercalcemia, and elevated calcium phosphorus product.

21. A pharmaceutical composition comprising:
   (a) from about 10% to about 40% by weight of cinacalcet HCl in an amount of from about 20 mg to about 100 mg;
   (b) from about 5% to about 10% by weight of starch;
   (b) from about 40% to about 75% by weight of microcrystalline cellulose,
   (c) from about 1% to about 5% by weight of povidone, and
   (d) from about 1% to 10% by weight of crospovidone,
   wherein the percentage by weight is relative to the total weight of the composition, and wherein the composition is for the treatment of at least one of hyperparathyroidism, hyperphosphonia, hypercalcemia, and elevated calcium phosphorus product.

22. The composition according to claim 21 further comprising from about 0.05% to about 1.5% by weight of colloidal silicon dioxide relative to the total weight of the composition.

23. The composition according to claim 21 further comprising from about 0.05% to about 1.5% by weight of magnesium stearate relative to the total weight of the composition.

\* \* \* \* \*